(12) United States Patent
Chin

(10) Patent No.: US 9,326,879 B2
(45) Date of Patent: May 3, 2016

(54) SYSTEMS AND METHODS FOR BARIATRIC THERAPY

(71) Applicant: Pavilion Medical Innovations, LLC, Norwell, MA (US)

(72) Inventor: Albert K. Chin, Palo Alto, CA (US)

(73) Assignee: Pavilion Medical Innovations, LLC, Norwell, MA (US)

( * ) Notice: Subject to any disclaimer, the term of this patent is extended or adjusted under 35 U.S.C. 154(b) by 343 days.

(21) Appl. No.: 13/923,948

(22) Filed: Jun. 21, 2013

(65) Prior Publication Data

US 2014/0012178 A1    Jan. 9, 2014

Related U.S. Application Data

(62) Division of application No. 13/007,344, filed on Jan. 14, 2011, now Pat. No. 8,491,519.

(60) Provisional application No. 61/295,012, filed on Jan. 14, 2010, provisional application No. 61/300,663, filed on Feb. 2, 2010, provisional application No. 61/360,653, filed on Jul. 1, 2010.

(51) Int. Cl.
*A61M 5/00* (2006.01)
*A61F 5/00* (2006.01)
*A61F 2/04* (2013.01)

(52) U.S. Cl.
CPC ............... *A61F 5/0076* (2013.01); *A61F 2/04* (2013.01); *A61F 5/0089* (2013.01); *A61F 2002/045* (2013.01)

(58) Field of Classification Search
CPC ... A61F 5/0076; A61F 5/0089; A61F 5/0013; A61F 5/0073; A61F 5/0083; A61F 5/0003; A61F 5/003; A61F 2/04; A61F 2/95; A61F 2002/044; A61F 2002/045
See application file for complete search history.

(56) References Cited

U.S. PATENT DOCUMENTS 4,493,711 A    1/1985  Chin et al.
4,630,609 A *  12/1986  Chin .............................. 606/194

(Continued)

FOREIGN PATENT DOCUMENTS

WO    2004049982    6/2004
WO    2005/060869   7/2005

(Continued)

OTHER PUBLICATIONS

Extended European Search Report for European Application EP 12 77 6288 Mailed Sep. 25, 2014.

(Continued)

*Primary Examiner* — Philip R Wiest
*Assistant Examiner* — Ariana Zimbouski
(74) *Attorney, Agent, or Firm* — Greenberg Traurig, LLP; Chinh H. Pham; Roman Fayerberg

(57) ABSTRACT

The present invention provides bariatric therapy systems. One system includes a gastrointestinal implant device and a delivery mechanism therefor. The device can include a sleeve for placement into a small intestine and to minimize absorption of nutrients by its walls. An anchoring mechanism coupled to a proximal end of the sleeve and designed to be secured within the stomach can be provided. A passageway extending through the anchoring mechanism and the sleeve can also be provided, along which food can be directed from the stomach to the small intestine. The delivery mechanism can include a housing for accommodating the device, and a deploying balloon situated within the housing and which can be actuated to direct the sleeve of the device from within the housing to the site of implantation. Methods for providing bariatric therapy are also provided by the present invention.

8 Claims, 10 Drawing Sheets

(56) References Cited

U.S. PATENT DOCUMENTS

| | | |
|---|---|---|
| 4,899,747 A | 2/1990 | Garren et al. |
| 5,820,584 A | 10/1998 | Crabb |
| 7,025,791 B2 | 4/2006 | Levine et al. |
| 7,347,875 B2 | 3/2008 | Levine et al. |
| 7,608,114 B2 | 10/2009 | Levine et al. |
| 7,794,447 B2 | 9/2010 | Dann et al. |
| 7,803,195 B2 | 9/2010 | Levy et al. |
| 7,837,643 B2 | 11/2010 | Levine et al. |
| 7,931,693 B2 * | 4/2011 | Binmoeller ............ 623/23.64 |
| 7,967,798 B2 * | 6/2011 | Reydel et al. ............ 604/271 |
| 2004/0220682 A1 | 11/2004 | Levine et al. |
| 2005/0049718 A1 | 3/2005 | Dann et al. |
| 2005/0096750 A1 | 5/2005 | Kagan et al. |
| 2005/0125075 A1 * | 6/2005 | Meade et al. ............ 623/23.64 |
| 2005/0273060 A1 | 12/2005 | Levy et al. |
| 2006/0009858 A1 | 1/2006 | Levine et al. |
| 2006/0161265 A1 | 7/2006 | Levine et al. |
| 2006/0173422 A1 | 8/2006 | Reydel et al. |
| 2007/0032879 A1 | 2/2007 | Levine et al. |
| 2007/0106213 A1 | 5/2007 | Spera et al. |
| 2007/0179335 A1 | 8/2007 | Gertner et al. |
| 2008/0109086 A1 | 5/2008 | Voegele et al. |
| 2008/0255678 A1 * | 10/2008 | Cully et al. ............ 623/23.65 |
| 2008/0262523 A1 | 10/2008 | Makower et al. |
| 2009/0255544 A1 | 10/2009 | Cox |
| 2011/0046537 A1 | 2/2011 | Errico |

FOREIGN PATENT DOCUMENTS

| | | |
|---|---|---|
| WO | 2005/065412 | 7/2005 |
| WO | 2010074712 | 7/2010 |
| WO | 2010/115011 | 10/2010 |

OTHER PUBLICATIONS

Gersin et al., "Duodenal—Jejunal Bypass Sleeve: A Totally Endoscopic Device for the Treatment of Morbid Obesity", Surgical Innovation, 14(4): 275-278 (2007).

International Search Report based on International Application No. PCT/US2011/021383 mailed Mar. 21, 2011.

International Search Report based on International Application No. PCT/US2012/033876 mailed Aug. 8, 2012.

Office Action issued in U.S. Appl. No. 13/007,344 mailed on Sep. 17, 2012.

Office Action issued in Chinese Application No. 201180008173.2 issued on Jun. 5, 2014.

* cited by examiner

SYSTEMS AND METHODS FOR BARIATRIC THERAPY

RELATED APPLICATIONS

This application is a divisional application of U.S. application Ser. No. 13/007,344 filed Jan. 14, 2011, which claims priority to and the benefit of U.S. Provisional Application No. 61/295,012 filed Jan. 14, 2010, U.S. Provisional Application No. 61/300,663 filed Feb. 2, 2010, and U.S. Provisional Application No. 61/360,653 filed Jul. 1, 2010, which applications are incorporated herein by reference in their entireties.

This application is also related to U.S. application Ser. No. 13/089,722, filed on Apr. 19, 2011, which application is incorporated herein by reference in its entirety.

BACKGROUND

According to the Center for Disease Control (CDC), over sixty percent of the United States population is overweight, and almost twenty percent are obese. This translates into about 38.8 million adults in the United States with a Body Mass Index (BMI) of 30 or above. The BMI is generally defined as the weight (e.g., in kilograms) of an individual divided by the height (e.g., in meters) of the individual, squared. To be considered clinically, morbidly obese, one must meet one of three criteria: BMI over 35, 100 lbs. overweight, or 100% above ideal body weight. There is also a category for the super-obese for those weighing over 350 lbs.

Obesity is thus an overwhelming health problem in the U.S. Moreover, because of the enormous strain associated with carrying this excess weight, organs are affected, as are the nervous and circulatory systems in an individual who is overweight or obese. In 2000, the National Institute of Diabetes, Digestive and Kidney Diseases (NIDDK) estimated that there were 280,000 deaths directly related to obesity. The NIDDK further estimated that the direct cost of healthcare in the US associated with obesity is $51 billion. In addition, Americans spend approximately $33 billion per year on weight loss products. In spite of this economic cost and consumer commitment, the prevalence of obesity continues to rise at alarming rates. From 1991 to 2000, obesity in the US grew by about 61%. Not exclusively a US problem, worldwide obesity ranges are also increasing dramatically.

There have been many attempts in the past to surgically modify anatomies of a patient to address the consumption problem by reducing the desire to eat. Stomach staplings, or gastroplasties, in order to reduce the volumetric size of the stomach, therein achieving faster satiety, were initially performed in the 1980's and early 1990's. Although able to achieve early weight loss, sustained reduction in connection with gastroplasties was not obtained. The reasons are not all known, but are believed to be related to several factors. One of which is that the stomach stretches over time, thereby increasing volume, while psychological drivers motivate patients to find creative approaches to literally eat around the smaller pouch.

Space-occupying gastric balloons have also been used to treat obesity since the 1980's. One such balloon is described by Garren et al. (U.S. Pat. No. 4,899,747 Method and apparatus for treating obesity). Gastric balloons are generally designed to decrease the functional volume of the stomach.

Similarly, intestinal sleeves are also being used for obesity treatment (Levine et al., U.S. Pat. No. 7,347,875 Methods of treatment using a bariatric sleeve; Levine et al. U.S. Pat. No. 7,025,791 Bariatric sleeve). These sleeves consist of an anchoring mechanism that attaches at one end of a thin walled plastic sleeve and extends from the pylorus to allow the sleeve to extend past the Ligament of Treitz. Intestinal sleeves function to decrease absorption from the portion of bowel covered by the sleeve. Presently, a guidewire is advanced into the patient's jejunum under fluoroscopic guidance (Gersin K S, Keller J E, Stefanidis D, et al. Duodenal jejuna bypass sleeve: A totally endoscopic device for the treatment of morbid obesity. Surg Innov 2007:14; 275). A gastroscope is then used to deploy the stent-like anchor in the pylorus, and gastroscopic instruments; e.g. graspers, are used to hold the sheath and advance it along the intestine to the Ligament of Treitz. However, complications often associate with delivery of intestinal sleeves. In addition, the sleeves are difficult to manipulate, and especially the current methods for advancing the sleeves along the intestine are time consuming and inefficient.

In another approach, an open bariatric surgical procedure known as the "Roux-en-Y" procedure, a small stomach pouch is created by stapling part of the stomach together.

This small pouch can limit how much food an individual can eat. In addition, a Y-shaped section of the small intestine is attached to the pouch to allow food to bypass the duodenum as well as the first portion of the jejunum. This causes reduced calorie and nutrient absorption. Common problems associated with Roux-en-Y include pouch stretching, where the stomach gets bigger overtime and can stretch back to its original size over time; a breakdown of staple lines where the staples fall apart and reverse the procedure; and a leakage of stomach contents into the abdomen (this is dangerous because the acid can eat away other organs. In addition, as the Roux-en-Y procedure requires open surgery, it is a painful, time-consuming operation and requires relatively long recovery time.

Accordingly, it would be desirable to have an effective system for bariatric therapy, reducing the harmful side effects such as painful surgical operations. In particular, there is a need for effective systems and delivery mechanisms for bariatric therapy that can minimize complications and recovery time, reduce operation time and resources, and improve therapy efficiency, success rate, and safety.

SUMMARY OF THE INVENTION

Figure 1A:
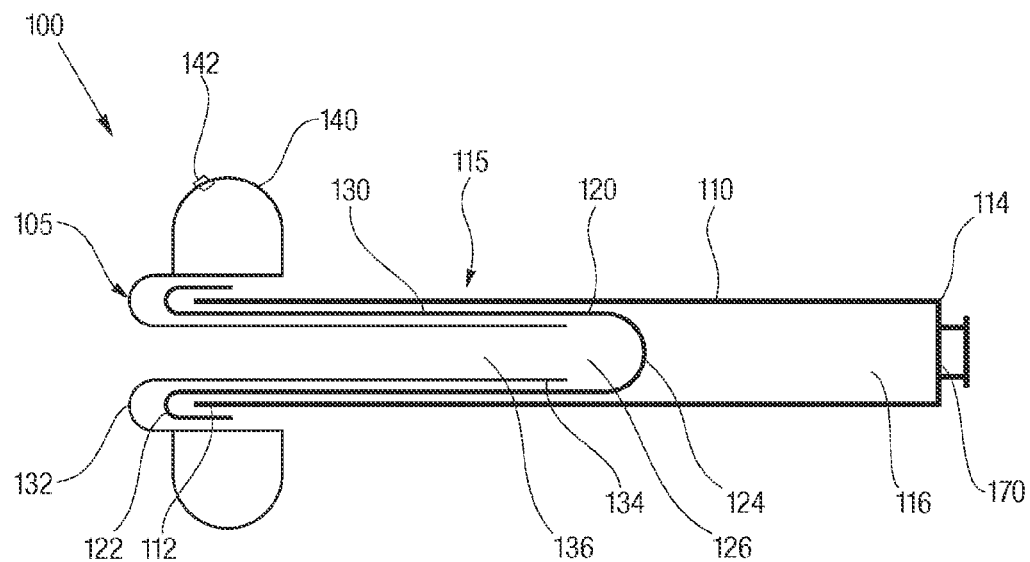
FIGS. 1A-1B illustrate an Intestinal Sleeve Delivery system in accordance with an embodiment of the present invention.

The present invention provides, in an embodiment, a gastrointestinal implant device. The gastrointestinal implant device can include a sleeve for placement into a small intestine and to minimize absorption of nutrients by a wall of the small intestine. The sleeve, in an embodiment, may be made from a sufficiently flexible material to permit the sleeve to move between an inverted position and an everted position. In certain embodiments, the sleeve may be made from a material having substantially low permeability, so as to minimize absorption of nutrients from the digested food by the wall of the small intestine. The gastrointestinal implant device, in an embodiment, can also include an anchoring mechanism coupled to a proximal end of the sleeve and designed to be secured within a stomach, so as to allow the sleeve to securely extend into the small intestine. In some embodiments, the anchoring mechanism is designed to reduce functional volume of the stomach. The anchoring mechanism, in one example, can be an inflatable balloon sufficiently large to prevent the inflatable balloon from entry into the small intestine. To that end, the anchoring mechanism may include a port for inflating the anchoring mechanism. The anchoring mechanism may alternatively be a self-expanding frame which, upon expansion, can be substantially frustoconical in shape for securing against a wall of the stomach, while allowing the stomach to maintain a substantially full functional volume. The gastrointestinal implant device, in an embodiment, can further include a passageway extending through the anchoring mechanism and the sleeve, and along which digested food can be directed from the stomach into the small intestine.

The present invention further provides, in another embodiment, a bariatric therapy system. The system can include a gastrointestinal implant device. The device, in an embodiment, can include a sleeve for placement into a small intestine and to minimize absorption of nutrients by a wall of the small intestine. The device can also include an anchoring mechanism coupled to a proximal end of the sleeve and designed to be secured within a stomach so as to allow the sleeve to securely extend into the small intestine. In some embodiments, the anchoring mechanism can be an inflatable balloon designed to reduce functional volume of the stomach upon inflation and may be designed to include a port for inflating the anchoring mechanism. The anchoring mechanism, in certain embodiments, can also be a self-expanding frame which, upon expansion, can be substantially frustoconical in shape for securing against a wall of the stomach while allowing the stomach to maintain a substantially full functional volume. The device can further include a passageway extending through the anchoring mechanism and the sleeve, and along which digested food can be directed from the stomach to the small intestine. In addition to the device, the system can further include a delivery mechanism for directing the device to a site of implantation. The delivery mechanism, in an embodiment, can include a housing for accommodating the device. The housing can be provided with a delivery end, an opposing proximal end, and a passageway therebetween. In certain embodiments, the housing can be substantially tubular in shape and/or made from a sufficiently flexible material for accommodating the device. The delivery mechanism, in an embodiment, can also include a deploying balloon, situated within the passageway of the housing, for accommodating the sleeve of the device. The balloon may be provided with an open end attached to the delivery end of the housing and a closed end situated within the housing, such that in the presence of positive pressure within the passageway of the housing, the balloon can be everted from within the housing to direct the sleeve of the device into the small intestine. A port, in an example, can be provided on the housing through which positive pressure can be introduced into the housing. The port, in an embodiment, can be provided with an inflation device detachably connected thereto. In addition, a gastroscope for guiding the system to the site of implantation can also be provided for use in connection with the system of the present invention.

The present invention also provides, in another embodiment, a delivery mechanism. The delivery mechanism can include a housing. The housing can be provided with a delivery end, an opposing proximal end, and a passageway therebetween. The delivery mechanism, in an embodiment, can also include a deploying balloon, situated within the passageway of the housing, for accommodating a sleeve of an implant device. The balloon may be provided with an open end attached to the delivery end of the housing and a closed end situated within the housing, such that in the presence of positive pressure within the passageway of the housing, the balloon can be everted from within the housing to direct the sleeve of the device into the small intestine. In some embodiments, the housing can be a reservoir capable of expanding to permit eversion of the balloon from within the passageway of the housing. In certain embodiments, the delivery mechanism can further include a port through which positive pressure can be introduced into the passageway of the housing to evert the balloon from within the passageway. To that end, the delivery mechanism may further include an inflation device detachably connected to the port and designed to introduce positive pressure into the housing via the port to deploy the implant device. In addition, a gastroscope for guiding the delivery mechanism to the site of implantation can also be provided for use in connection with the delivery mechanism of the present invention.

The present invention additionally provides, in another embodiment, a method for providing bariatric therapy. The method can include everting a sleeve from an inverted position into a small intestine. In an embodiment, positive pressure can be used to cause eversion of the sleeve. The method can further include anchoring the sleeve at its proximal end adjacent a pyloric junction between stomach and mall intestine. The anchoring step, in an embodiment, can include securing an anchoring mechanism coupled to a proximal end of the sleeve within the stomach so as to allow the sleeve to securely extend into the small intestine. The method, in some embodiments, can further include allowing digested food to be directed from the stomach through the anchoring mechanism into the sleeve, while minimizing absorption of nutrients from the digested food by a wall of the small intestine. In addition, to the extend desired, the method can further include guiding the sleeve to a site of implantation with a gastroscope.

DESCRIPTION OF SPECIFIC EMBODIMENTS

In accordance with one embodiment of the present invention, a system is provided herein for bariatric therapy. One system, as described hereinafter, may be used to employ volume restriction within the stomach and/or enhance malabsorption within the small intestine. Such a system of the present invention includes, in one embodiment, a gastrointestinal implant device having an anchoring mechanism designed to be positioned within the stomach to anchor the device, and an intestinal sleeve attached at one end to the anchoring mechanism. The sleeve can be designed to extend along a portion of the small intestine to minimize or prevent nutrient absorption by the small intestine. In one embodiment, the anchoring mechanism may be a space occupying ring, an inflatable balloon, a self-expanding anchor or frame, or any combination thereof. As will be seen hereinafter, the system can also include a delivery mechanism for delivering or placing the device at a site of implantation.

Generally, food to be digested enters the stomach through the cardiac orifice from the esophagus. Once in the stomach, food is at least partially digested to produce chyme, a semifluid substance that can be homogeneous, creamy or gruel-like. Once produced, the chyme can then exit the stomach through the pylorus or pyloric junction and enter the small intestine. The pylorus is a distal aperture of the stomach surrounded by a strong band of circular muscle. The small intestine, about nine feet in length, is a convoluted tube, extending from the pylorus to the ileo-caecal valve where it terminates in the large intestine. The small intestine has three sections including the duodenum, jejunum and the ileum.

The duodenum has four sections including the superior, descending, transverse and ascending sections which typically form a U-shape. The superior section is about two inches long and ends at the neck of the gall bladder. The descending section is about three to four inches long and includes a nipple shaped structure (papilla of vater) through which pancreatic juice from the pancreas and bile produced by the liver and stored by the gall bladder can enter the duodenum from the pancreatic duct. The pancreatic juice typically contains enzymes essential to protein digestion and bile that can be used to dissolve the products of fat digestion. The ascending section, on the other hand, is about two inches long and forms the duodenal-jejunal flexure where it joins the jejunum, the next section of the small intestine. The duodenal-jejunal flexure is fixed to the ligament of Treitz (musculus supensionus duodeni). The juices secreted in the duodenum can break the partially digested food down into particles small enough to be absorbed by the body.

Referring now to FIG. 1A, a system 100 for providing bariatric therapy according to one embodiment of the present invention is shown. System 100 may include a gastrointestinal implant device 105 for facilitating weight loss. In one embodiment, the device 105 can be used to reduce the size of the stomach while simultaneously reducing absorption of food nutrients within the small intestine. In accordance to an embodiment of the present invention, the device 105 may include an intestinal sleeve 130 designed to extend from within the stomach and along a portion of the intestine below the pylorus, to minimize absorption of nutrients by the intestinal walls.

As illustrated, the sleeve 130 may include a proximal end 132 that may be designed for placement adjacent the pyloric junction, an area around the pylorus where the stomach and the small intestine meet. The sleeve 130 may further include a passageway 136 extending from the proximal end 132 to allow passage of food and other food material through sleeve 130. As used herein, "food" or "other food material" can be used interchangeably; "food" can also include undigested, partially digested, and completely digested food. The sleeve 130 may further include a distal end 134. The distal end 134, in an embodiment, can be open-ended to provide an opening through which food and other food material can exit sleeve 130.

The sleeve 130, in an embodiment, can be designed to reduce absorption and digestion of food by the intestinal walls. In particular, sleeve 130 can line and cover the intestinal wall, and act to reduce absorption and digestion of food by delaying the mixing of food with bile and pancreatic juices until after the food exits the distal end 134 of sleeve 130. In other words, by preventing the mixing of bile and pancreatic juices with food in the duodenum, digested (partially or completely) food material is not broken down into particles small enough to be absorbed by the body. As a result, the absorption of nutrients (e.g., fats and carbohydrates) is reduced.

To that end, the sleeve 130 can be made from any material that can aid in the passage of food through the sleeve 130. In one embodiment, the sleeve 130 can be made from a material that minimizes resistance and friction so as to allow food to slide more easily through the sleeve. For instance, the sleeve 130 can be made from a material that is substantially smooth and/or has a relatively low coefficient of friction. The sleeve 130 material may further have substantially low permeability to fluids to minimize the occurrence of digested food leaking through the sleeve 130 and coming into contact with the intestinal wall where it can be absorbed. The sleeve 130 can also be made from any material that helps to minimize or prevent tissue in-growth, as well as a material that can be non-irritating to the bowel, so as to aid in the removal of the sleeve 130, once removal is desired. Since the sleeve 130 can be designed to be implanted within an intestine of a human or animal body, the sleeve 130 should also be made from a material that is biocompatible. The biocompatibility of the material may help minimize occurrence of adverse reactions due to constant contact of the sleeve 130 with the gastrointestinal tract. In an embodiment, the sleeve 130 can be made from any material that can be obtained commercially.

Should it be desired, sleeve 130 may further include a coating that can aid in reducing absorption of nutrients, minimize resistance to provide a smooth passageway for food, minimizing porosity, preventing tissue in-growth, allowing subsequent removal of the device from the intestinal tract, or any other characteristic that may be desirable for the sleeve 130. The coating may be applied to the sleeve 130 on an inner surface, an outer surface, or a combination thereof to minimize any porous characteristics of the sleeve material.

In one embodiment, the sleeve 130 can also be made from any material that allows the sleeve 130 to expand and collapse in accordance with the digestive process. When food enters and passes through the sleeve 130, the sleeve material can be such that it may allow the sleeve 130 to expand sufficiently to accommodate the digested food. Once the food from the stomach has passed through the sleeve 130, however, the sleeve material can be such that is may allow the sleeve 130 to become flexible or floppy, permitting the sleeve 130 to contour toward one side of the intestine. In this floppy state, the sleeve 130 may permit the pancreatic juice to flow with minimal resistance into the duodenum through the papilla of vater. Of course, in some instances, it may be desirable for the sleeve 130 to maintain a substantially constant form throughout the digestive process. In these instances, the sleeve 130 may be made from a material that can maintain such a substantially constant form.

The length of the sleeve 130 may, in an embodiment, vary depending on a variety of characteristics. In certain instances, the length of the sleeve 130 may be dependent on the patient's Body Mass Index (BMI). In other instances, the length of the sleeve 130 may be selected based on the amount of absorption desired. A longer sleeve 130, for example, may minimize absorption of nutrients by the intestinal walls over a longer distance than a shorter sleeve 130. In some instances, the length of the sleeve 130 may be selected based on the distance necessary to bypass the duodenum and allow the sleeve 130 to couple with the jejunum. It should be noted that the length of the sleeve 130 should also permit the sleeve 130 to fit within the delivery mechanism 115 as well as within the intestine.

The sleeve 130 may have any shape desirable, so long as the shape allows the sleeve 130 to fit within the intestine. In one embodiment, the sleeve 130 may have a substantially tubular shape to allow the sleeve 130 to substantially conform to the intestine. Of course, other geometric shapes may be possible.

The sleeve 130 may further have any diameter desirable so long as the diameter allows food to travel through the sleeve 130 without substantial hindrance. In one embodiment, the sleeve 130 may have a diameter to allow the sleeve 130 to substantially conform to the intestinal walls when in an expanded state. By substantially conforming to the intestinal walls in an expanded state, the sleeve 130 can maximize the amount of food traveling through. Of course, smaller diameters may also be possible.

The gastrointestinal implant device 105 may further include, in accordance with an embodiment of the present invention, an anchoring mechanism 140, coupled to the proximal end 132 of the sleeve 130. The anchoring mechanism 140 may be designed to be positioned, in certain instances, in the stomach to anchor the device 105 thereat. In an embodiment, the anchoring mechanism 140 can be an anchor that acts to reduce the functional volume of the stomach. An example of such an anchoring mechanism 140 can be a space occupying inflatable ring or balloon, or any other anchoring mechanism 140 adapted to adequately engage and secure the proximal end 132 of the sleeve 130 at the pyloric junction, while reducing the volume of the stomach. In an embodiment, the anchoring mechanism 140 can be integral with the sleeve 130 at the proximal end 132, so that the anchoring mechanism 140 and sleeve 130 are formed from one piece of material. Alternatively, the anchoring mechanism 140 can be separate and independent from the sleeve so that the anchoring mechanism and sleeve 130 are formed from two pieces of material and are coupled to one another.

Figure 1B:
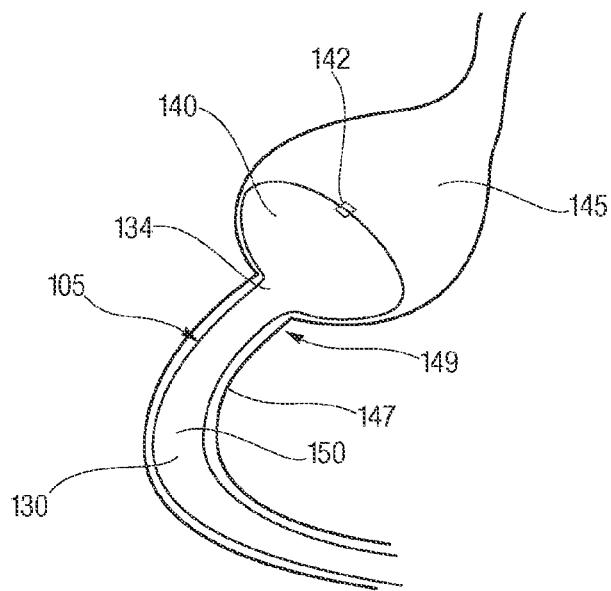

FIG. 1B shows the gastrointestinal implant device 105 in a deployed position. In particular, the anchoring mechanism 140 is positioned at a point within the stomach 145 just above the pylorus 149. The proximal end 134 of the sleeve 130, on the other hand, can extend from the anchoring mechanism 140 within the stomach 145, across the pylorus 149, and into the small intestine 147. It should be appreciated that anchoring mechanism 140 can also extend into the pylorus 149 and proximal end 134 of the sleeve 130 can be situated adjacent the pylorus 149. A passageway 150, in an embodiment, can extend through the anchoring mechanism 140 and the sleeve 130, so that food can be directed from the stomach 145, into the device 105 and moved along the passageway 150, and into the small intestine 147.

As noted, the anchoring mechanism 140 can be designed, in certain instances, to facilitate weight loss by reducing the functional volume of the stomach 145. In other words, by occupying a portion of the stomach 145, the anchoring mechanism 140 can act to decrease the functional volume of the stomach 145, and thus, the amount of food intake by the patient. To that end, The anchoring mechanism 140, in an embodiment, may have any size desirable, depending on the particular application, as the size of the anchoring mechanism 140 may affect the functional volume by which the stomach 145 is reduced. For instance, a larger anchoring mechanism 140 may occupy a larger space within the stomach and may, accordingly, reduce the functional volume of the stomach by a larger amount than a smaller anchoring mechanism. It should be noted that the size of the anchoring mechanism 140 needs to permit the anchoring mechanism 140 to be securely positioned within the stomach at a site of implantation. That is, the anchoring mechanism 140 can be sufficiently large to prevent it from entry into the small intestine.

The anchoring mechanism 140, as illustrated in FIGS. 1A-1B, may have a donut shape. A donut shape may allow the anchoring mechanism 140 to be positioned within the stomach, such that the anchoring mechanism 140 can substantially conform to the shape of the stomach and may, simultaneously, provide an exit for food to leave the stomach. Of course, other shapes for the anchoring mechanism 140 may be possible.

To adequately secure the anchoring mechanism 140 within the stomach, the anchoring mechanism 140 can be made from a material that can radially expand to exert a sufficient radial force to push the anchoring mechanism 140 against the walls of the stomach at the site of implantation. It should be appreciated that the material used should permit the anchoring mechanism 140 to conform to the dimensions of the stomach at the implantation site, even when the dimensions of the stomach vary. In one embodiment, an anti-inflammatory agent such as dexamethasone, prednisolone, corticosterone, budesonide, estrogen, sulfasalazine, mesalamine, or any suitable combination or mixture thereof may be applied to the anchoring mechanism 140 to prevent inflammation or any other adverse reaction caused by the engagement of the anchoring mechanism 140 within the stomach.

In accordance with one embodiment, as illustrated in FIGS. 1A-1B, the anchoring mechanism 140 may be provided with a port or valve 142 to which an inflation mechanism may be detachably connected for inflation purposes. To that end, the valve can be a one-way valve designed to prevent premature and unintentional deflation and removal of the device 105 from the intestinal tract. The one-way valve may be an elastomeric plug, a spring loaded valve, or any other valve known in the art as the present invention is not intended to be limited in this manner.

An inflation mechanism (not shown) for inflating the anchoring mechanism 140 can include, for instance, an inflation catheter or any other inflation device capable of inflating the anchoring mechanism 140. As the inflation mechanism can be detachably coupled to port or valve 142 of the anchoring mechanism 140, the inflation mechanism can be disconnected and detached from the port or valve 142 of anchoring mechanism 140 following inflation. It should be appreciated that the anchoring mechanism 140 can be deflated when removal of the device 105 is desired.

Connection of the inflation mechanism to port or valve 142 of the anchoring mechanism 140 may occur, in certain embodiments, through the use of a connector (not shown). The connector can act to couple the inflation mechanism to the anchoring mechanism 140 allowing the inflation mechanism to inflate the anchoring mechanism 140. In an embodiment, the connector may be situated on either the inflation mechanism or the anchoring mechanism 140. Alternatively, the connector may include a two-piece design having two complimentary pieces to permit coupling between the inflation mechanism and the anchoring mechanism 140. Examples of connectors include a mating luer connector, a metal tube, or any other connectors known in the art.

Although an inflation mechanism is described herein, it should be appreciated that the anchoring mechanism 140 can be self-expanding to allow expansion of anchoring mechanism 140 without the aid of additional inflation mechanisms. Such self-expanding mechanism, similar to a life vest, are known in the art.

Still referring to FIG. 1A, system 100 for providing bariatric therapy may further include, in an embodiment, a delivery mechanism 115 for delivering the gastrointestinal implant device 105 to a site of implantation. In an embodiment, the delivery mechanism 115 can include a housing 110 having a delivery end 112, an opposing end 114, and a passageway 116 therebetween. In one embodiment, the delivery end 112 can be designed to permit sleeve 130 of device 105 to be inserted (e.g., in an inverted position) into delivery mechanism 115. In addition, the delivery end 112 may be sufficiently sized to permit anchoring mechanism 140 to be securely positioned about delivery end 112.

In one embodiment, the housing 110 can be made from any material capable of passing through the intestine and delivering device 105 to a site of implantation. To that end, housing 110 may be formed from a substantially hard material, so as to minimize deformation of the housing 110 during delivery. Examples of materials that are substantially hard include metals, plastics, ceramics, or any other materials that can maintain a substantially consistent shape. Housing 110 can also be made from a sufficiently flexible material to permit compression of the housing 110. For example, housing 110 may be formed from a thin-walled membrane such as nylon laminated with polyurethane.

Since the housing 110 is designed to be inserted into an intestine of a human or animal body, the housing 110, in an embodiment, can be made from a material that is biocompatible. The biocompatibility of the material may help minimize occurrence of adverse reactions due to use of the housing 110 within an intestine. The housing 110 may further include a coating on an outer surface to reduce friction between the housing 110 and the intestinal wall upon insertion into the intestine. Likewise, the housing 110 may include a coating on an inner surface to reduce friction during deployment of the sleeve 130 situated within the housing 110.

It should be appreciated that the housing 110 may be provided with any shape desirable, depending on the particular application, as the shape of the housing 110 may affect ability of the housing 110 to deliver the device 105 to a site for implantation. For instance, housing 110 may be tubular in shape. Housing 110, in other embodiments, may be triangular in shape. Of course, other shapes can be used as the present invention is not intended to be limited in this manner.

The delivery mechanism 115, as shown in FIG. 1A, can also include a deploying balloon 120 for use in advancing the sleeve 130 of device 105 from within housing 110 to the site of implantation (e.g., stomach and/or small intestine). The deploying balloon 120, in an embodiment, may include an open end 122 and a closed end 124, and may be provided with a length sufficient to accommodate sleeve 130. In an embodiment, open end 122 of deploying balloon 120 can be provided with a tight fitting seal with the delivery end 112 of housing 110. By providing such a seal at the delivery end 112 of housing 110 and by providing the deploying balloon 120 with closed end 124, positive pressure can be introduced into the housing 110 to evert the deploying balloon 120 from within the housing 110, and to aid in deployment of the sleeve 130 from the deploying balloon 120. Of course, deploying balloon 120 and housing 110 can be integral to each other (e.g., as a one-piece design) where additional seal may not be necessary to keep positive pressure in the housing 110.

To deploy device 105 to a site of implantation, deploying balloon 120 can be made from a material capable of withstanding a sufficient force, so as to permit eversion of the deploying balloon 120, and thus advancement of the sleeve 130 from within the housing 110. In an embodiment, the deploying balloon 120 may be made from a thin-walled membrane. For example, the deploying balloon 120 may be made from nylon laminated with polyurethane or any similar materials. In an embodiment, the deploying balloon 120 may have a thickness ranging from about 0.05 mm to about 0.09 mm. In an embodiment, the thickness of the deploying balloon 120 may be about 0.076 mm or 0.003 inches. The material of the deploying balloon 120 may also be impermeable to fluids in order to allow the deploying balloon 120 to withstand sufficient positive pressure. Since the deploying balloon 120 is designed to be inserted within an intestine of a human or animal body, the deploying balloon 120 can be made from a material that is biocompatible. The biocompatibility of the material may help minimize occurrence of adverse reactions due to use of the deploying balloon 120 within an intestine.

Figure 2A:
FIGS. 2A-2B illustrate another Intestinal Sleeve Delivery system in accordance with an embodiment of the present invention.
Figure 2B:
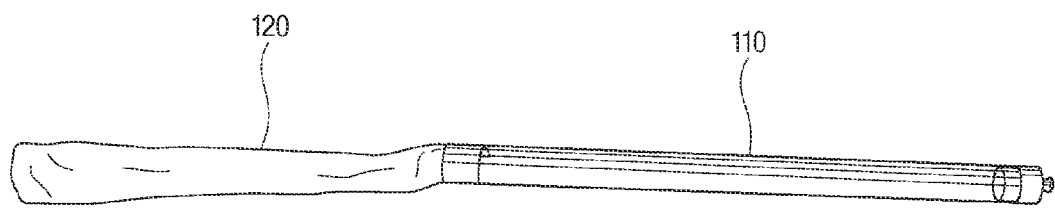

As shown in FIGS. 2A-2B, the housing 110 and the deploying balloon 120 can be integral with one another (FIG. 2A) or may be provided as two separated components (FIG. 2B). In the embodiment where housing 110 and deploying balloon 120 can be integral with one another, housing 110 and deploying balloon 120 can be made of the same material, e.g., a continuous sheet of the same sufficiently flexible material. This way, no attachment or connection mechanism is required for connecting housing 110 and deploying balloon 120. Suitable materials include without limitation, plastics, rubber, polymers, resin, cloth, and so on. Alternatively, in the embodiment where housing 110 and deploying balloon 120 can be two separate components, housing 110 and deploying balloon 120 can be made of different materials. For example, housing 110 can be made of a sufficiently rigid material, while the deploying balloon 120 being made of a sufficiently flexible material. Of course, the same material can be used for both the housing 110 and the deploying balloon 120. Suitable attachment or connection mechanism known in the art may also be provided, to the extent desired, so as to connect housing 110 and deploying balloon 120.

As shown in FIG. 2A, the housing 110 can have a diameter substantially smaller than that of the deploying balloon 120. In one example, the diameter of the housing 110 can be about half of the deploying balloon 120 while still able to accommodate the deploying balloon 120. In other examples (e.g., FIG. 2B), the housing 110 can have a diameter that is larger than that of the deploying balloon 120. It should be noted that FIGS. 2A-2B illustrate the deploying balloon 120 in its everted or deployed position, and that before eversion or deployment, the deploying balloon 120 can be inverted for placement within the housing 110. Of course, the diameter of the housing 110 and deploying balloon 120 may remain substantially constant throughout.

It should be appreciated that regardless of the size of the housing 110 relative to that of the deploying balloon 120, the diameter of each should be sufficient to accommodate the sleeve 130. It should be appreciated that the length of the housing 110 should permit the delivery mechanism 115 to be inserted into an intestine and advanced along the intestine to a site for implantation.

The housing 110, in an embodiment, may have any shape desirable, depending on the particular application, as the shape of housing 110 can facilitate delivery of the device 105 to a site for implantation. For instance, housing 110 may be tubular in shape. Of course, other shapes can be used as the present invention is not intended to be limited in this manner.

In accordance with one embodiment, the delivery mechanism 115 can further include an inflation mechanism (such as inflation device 250 shown in FIG. 4) for introducing positive pressure into the housing 110, so as to cause eversion of the deploying balloon 120 from within the housing 110. Suitable inflation mechanism can include, for instance, an inflation catheter, a pump, or any other inflation device capable of introducing positive pressure the housing 110. As the inflation mechanism can be detachably coupled to the housing 110, the inflation mechanism can be disconnected and detached from the housing 110 following inflation. Connection of the inflation mechanism to the housing 110 may be achieved using any method known in the art.

In order to introduce positive pressure into housing 110 through the use of an inflatable mechanism, the system 100 of the present invention may be provided with an inflation port 170 in the housing 110 through which fluids (e.g., air, liquids, gas or other substances) can enter with sufficient positive pressure to evert deploying balloon 120 and subsequently deploy the gastrointestinal implant device 105. In one embodiment, inflation port 170 can be situated at end 114 of housing 110. Of course, other locations for the inflation port 170 may be possible, as long as fluids can enter with a sufficient force to deploy the device 105.

Figure 3A:
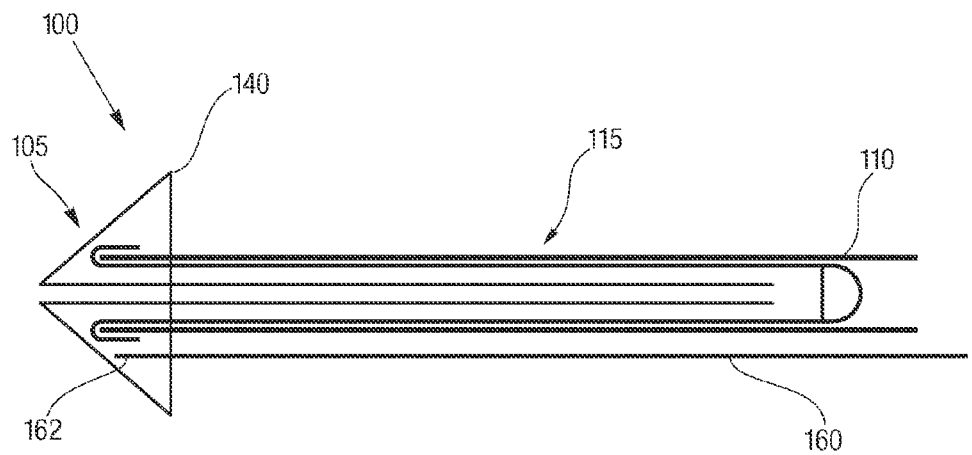
FIGS. 3A-3B illustrate an Intestinal Sleeve Delivery system from an everted position to a deployed position in accordance with an embodiment of the present invention.
Figure 3B:
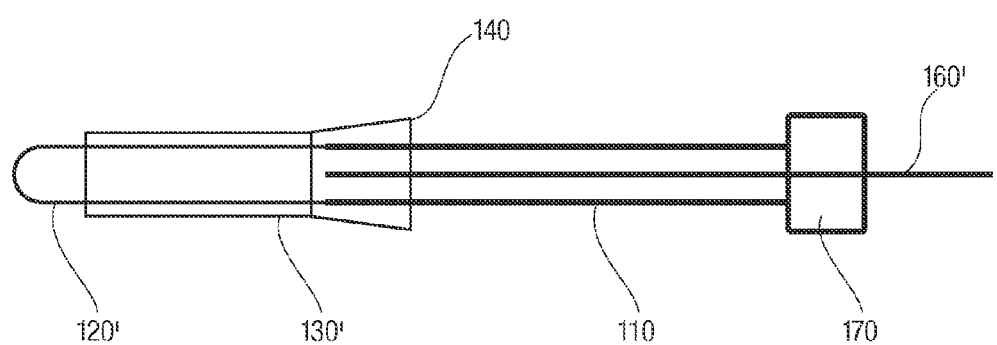

Now referring to FIGS. 3A-3B, the system 100 of the present invention can be used in connection with a gastroscope 160, 160'. The gastroscope 160, 160' may help guide the system 100 through the gastrointestinal tract. In an embodiment, the gastroscope 160 in FIG. 3A may be provided with a body designed to be situated about or adjacent the housing 110. The gastroscope 160 may also be provided with tip 162 to be positioned against a surface of the anchoring mechanism 140. In such an embodiment, the anchoring mechanism 140 may be constructed of transparent material to allow visualization out the end of the gastroscope 160 as shown in FIG. 3A. No X-ray exposure or any other mechanism may be needed to help deploy the gastrointestinal implant device 105 of the present invention. Should it be desired, delivery mechanism 115 and device 105 may include an opaque substance to permit visualization by a user during implantation.

In certain embodiments, the system 100 of the present invention may be designed to allow a gastroscope 160' to help guide the system 100 through the intestinal tract. As shown in FIG. 3B, gastroscope 160' may be used with the deploying balloon 120' and sleeve 130' in their everted or deployed position to help guide the sleeve 130' to its desired location (e.g., to further extend along the small intestine). The gastroscope 160', as shown, may be positioned through the housing 110 and beyond and designed to maintain the stability of the system 100 as the system 100 is advanced along the gastrointestinal tract. It should be noted that while the gastroscope 160 can be positioned in any manner to allow guidance of the system 100, its design should minimize any obstructions of the deploying balloon 120 and sleeve 130 from everting. In an embodiment, the gastroscope 160 may be any guidewire that is commercially available.

Figure 4:
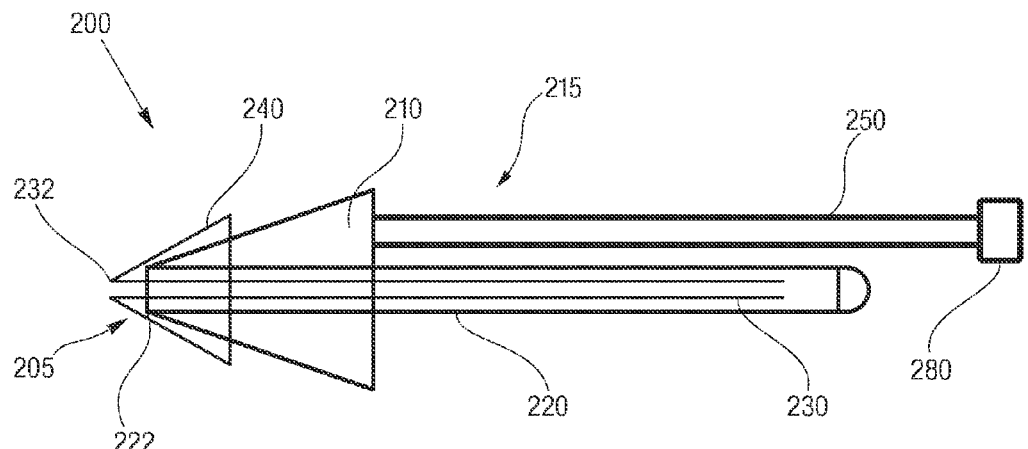
FIG. 4 illustrates still another Intestinal Sleeve Delivery system in accordance with an embodiment of the present invention.
Figure 5A:
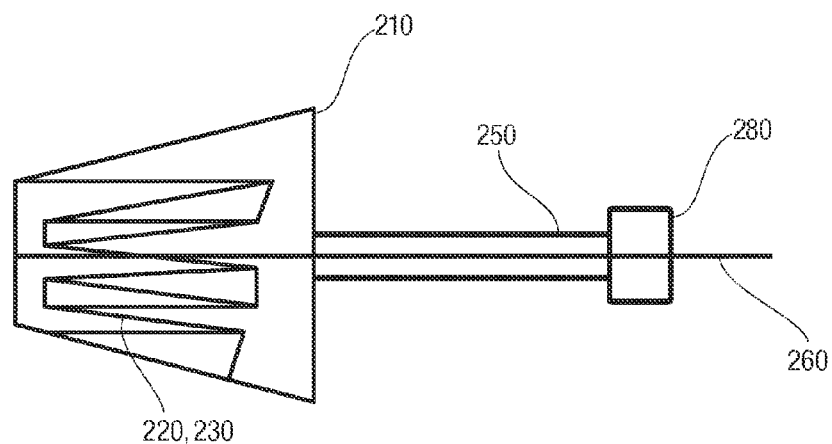
FIGS. 5A-5B illustrate a further Intestinal Sleeve Delivery system from an everted position to a deployed position in accordance with an embodiment of the present invention.
Figure 5B:
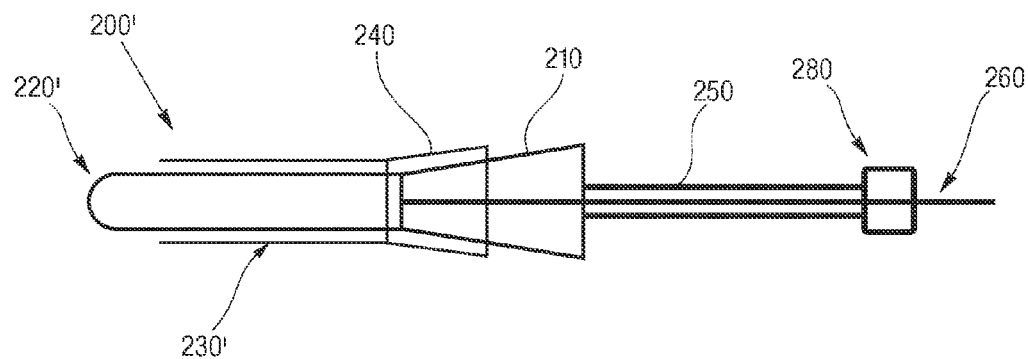
Figure 6:
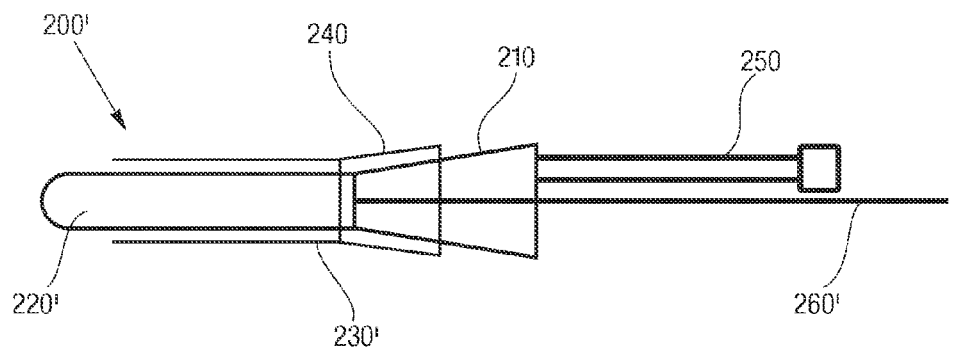
FIG. 6 illustrates still a further Intestinal Sleeve Delivery system in a deployed position in accordance with an embodiment of the present invention.

Looking now at FIGS. 4-6, there are illustrated alternative system of the present invention. As illustrated, system 200 can be used to provide bariatric therapy. System 200, in an embodiment, can include a delivery mechanism 215 and an implant device 205. In accordance with the embodiments shown in FIGS. 4-6, delivery mechanism 215 may be substantially similar to the delivery mechanism 115 described above, but the housing 110 delivery mechanism 215 may be a reservoir 210 for use in connection with the deployment of the device 205. Such a housing 210 can allow the delivery mechanism 215 to reside in different organs, such as the stomach in a patient, in addition to being inserted into the intestine. The delivery mechanism 215, in accordance with one embodiment, may include a reservoir 210 for use in connection with implantation of device 205. In one embodiment, the reservoir 210 may serve substantially the same functions as housing 110 in that the reservoir 210 can be used to accommodate at least a part of the device 205 and deliver the device 205 to a site for implantation. Reservoir 210, if desired, may be designed to accommodate sleeve 230 in reservoir 210 and may be designed to facilitate eversion of sleeve 230.

In an embodiment, the reservoir 210 can be made from a material that can be sufficiently strong to allow the reservoir 210 to be directed within the body of a patient without rupturing. The material, in an embodiment, can also be sufficiently flexible to allow the reservoir 210 to expand and collapse during deployment of the device 205.

The reservoir 210 may have any shape, as long as the shape can fit within the intestine or esophagus for delivery. In an embodiment, the reservoir 210 can be substantially circular in shape and can be expanded to any shape desired. In another embodiment, the reservoir 210 can be tubular in shape. Of course, other shapes are possible. The reservoir 210, in another embodiment, may have a size and/or length sufficient to accommodate balloon 220 and/or sleeve 230. As shown in FIG. 5A, the size and/or length of the reservoir 210 may be such that it may accommodate balloon 220 and/or sleeve 230 in a folded or rolled up manner.

The reservoir 210 may also be provided with any size desirable, as the size the reservoir 210 may facilitate delivery of device 205 and sleeve 230. For example, a smaller sized reservoir 210 may be used to deliver device 205 through an individual's esophagus, while a larger one may not be able to fit through an esophagus.

The delivery mechanism 215, in an embodiment, may further include a deploying balloon 220, similar to deploying balloon 120, for use in placement of the device 205 at the site of implantation within the gastrointestinal tract. It should be noted that the length and shape of the deploying balloon 220 should be such that the balloon 220 can fit (e.g., in a folded or rolled up manner), at least partially within the reservoir 210. In an embodiment, the balloon 220 can be attached to or positioned about an end of the reservoir 210 at its open end 222.

A sleeve 230 may be stored (e.g., in an inverted state) within deploying balloon 220 similar to the manner in which the sleeve 130 can be stored within deploying balloon 120 and housing 110, as described above. In an embodiment, the sleeve 230 may be stored in a folded state such as shown in FIG. 5A or may be stored in a rolled up state. Of course, the sleeve 230 may be stored in other manners so long as it fits, at least partially within the reservoir 210. An anchoring mechanism 240 for anchoring and securing device 205 to a site of implantation, similar to the one described above, may be situated at the proximal end 232 of sleeve 230, as shown in FIG. 4.

To deploy the gastrointestinal implant device 205, an inflation device 250 may be connected to the reservoir 210. The inflation device 250, in an embodiment, may be designed so as to permit insertion of the gastrointestinal implant device 205 through the esophagus of a patient. In an embodiment, the inflation device 250 can be sufficiently thin and narrow. A seal 280, can be provided at the end of the inflation device 250, as desired, to minimize leakage of fluid being introduced by inflation device 250.

FIGS. 5A, 5B, and 6 show the use of a gastroscope 260 to help guide the system 200 through the intestinal tract to a site of interest. The gastroscope 260, as shown in FIG. 5A, can be positioned through the inflation device 250 and the reservoir 210. In another embodiment shown in FIG. 6, gastroscope 260' can extend to reservoir 210 without going through the inflation device 250. It should be noted that FIGS. 5B and 6 show the system 200' in a fully deployed state, with the deploying balloon 220' and sleeve 230' in their everted position.

To prepare the system 100 for insertion in the body, a user can initially position a deploying balloon 120 within housing 110 of delivery mechanism 115. In one embodiment, the open end 122 of the deploying balloon 120 can be situated adjacent or attached to the delivery end 112 of the housing 110, and the closed end 124 of the deploying balloon 120 can be situated adjacent the opposing end 114 of the housing 110. An open ended sleeve 130 may then be placed within cavity 126 of deploying balloon 120 with the open ended distal end 134 of the sleeve 130 situated adjacent the closed end 124 of the deploying balloon 120, while the proximal end 132 of the sleeve 130 situated adjacent the open end 122 of the deploying balloon 120. Additionally, anchoring mechanism 140, being coupled to the proximal end 132 of the sleeve 130, can be positioned about the delivery end 112 of the housing 110.

Once loaded, the system 100 may be inserted into the body, and advanced along the intestine within the body to a site of interest for implantation. A gastroscope 160 may be used to help guide the system 100 through the intestinal tract to a site of implantation. In an embodiment, a guidewire (not shown) may be used to maintain the stability of the system 100 as the system 100 advances through the tract. Once at the site of implantation, the system 100 can be prepared for deploying the device 105. Implantation may first require the anchoring mechanism 140, attached to the proximal end 132 of the sleeve 130, to be inflated using an inflation mechanism. Inflation of the anchoring mechanism 140 can act to hold the gastrointestinal implant device 105 in a desired position during the eversion process. For example, the anchoring mechanism 140 can be placed within the stomach or in the small intestine adjacent the pyloric junction. After the anchoring mechanism 140 is anchored at the site of interest, the sleeve 130 may be everted. Eversion may require the direction of pressurized or unpressurized fluid (e.g., gas, liquid, or a combination thereof) into housing 110 via inflation port 170. As fluid is directed into housing 110, the fluid acts to evert and advance deploying balloon 120 from within housing 110, while pushing sleeve 130 from housing 110 along with deploying balloon 120, as shown in FIG. 3B. In some embodiments, the sleeve 130 is a shorter length than the deploying balloon 120, which can allow complete delivery of the sleeve 130 upon full eversion of deploying balloon 120.

Figure 7:
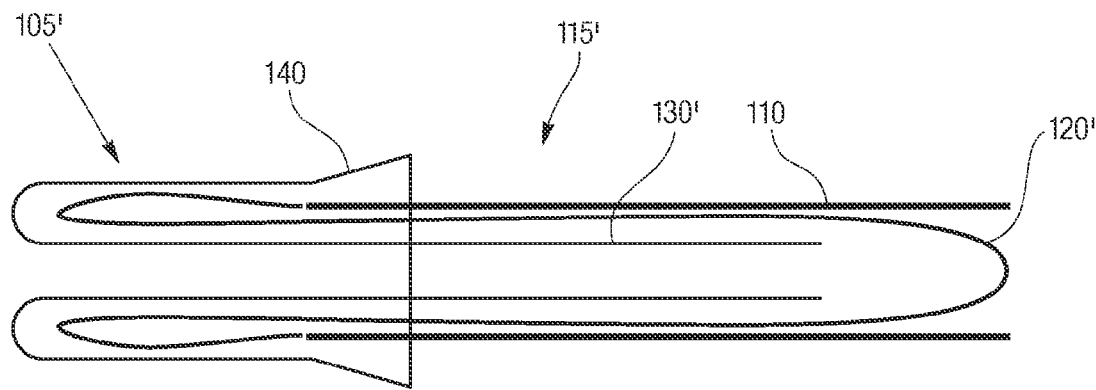
FIGS. 7-8 illustrate various stages of everting a Intestinal Sleeve Delivery system in accordance with an embodiment of the present invention.
Figure 8:
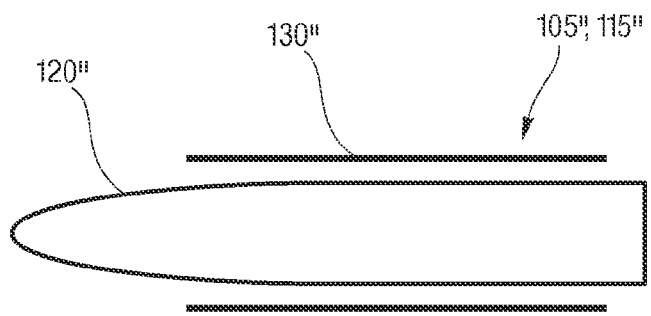

FIG. 7-8 show the deploying balloon 120 and sleeve 130 of the system 100 in partial eversion and subsequent deployment upon full eversion. In FIG. 7, gastrointestinal implant device 105' is in the process of being everted from within the passageway 116 of the housing 110, where everting deploying balloon 120' pushes and everts the sleeve 130' from therewithin. The everting deploying balloon 120', thereafter, can distend the intestine as it is deploying the everting sleeve 130', and can automatically follow the course of the bowel. FIG. 8 shows the implant device 105" in a fully deployed state, with everted deploying balloon 120" extending beyond the everted sleeve 130". With the gastrointestinal implant device 105" deployed and engaged within the intestinal wall, food and other food material can be passed from the stomach through the everted sleeve 130".

In accordance with the embodiments depicted in FIGS. 4-6, the method of deploying device 205 using a reservoir 210 may be substantially similar to the method described above with several changes to reflect the use of a reservoir 210. Once loaded into the reservoir 210, system 200 may be inserted into the body, and advanced along the intestine within the body to a site of implantation. A gastroscope 260 may be used to guide the system 200 through the gastrointestinal tract. Implantation may first require the anchoring mechanism 240, attached to the proximal end 232 of the sleeve 230, to be inflated using an inflation mechanism. After the anchoring mechanism 240 is anchored to the stomach or small intestine at the site of implantation, the device 205 may be everted. Eversion may require activation of the inflation device 250, which can result in the reservoir 210 being inflated, as shown in FIG. 5A. Inflation of the reservoir 210 can cause the reservoir 210 to enlarge and/or become pressurized, allowing the balloon 220 to evert and deploy the device 205. FIGS. 5B and 6 show embodiments of the system 200 in a fully deployed state. In an embodiment, the reservoir 210 can provide a low friction compartment for everting the balloon 220 and sleeve 230.

Following deployment of the sleeve 130, the deploying balloon 120 can be deflated and a vacuum can be drawn to constrict the deploying balloon 120. Constriction of the deploying balloon 120 can allow the deploying balloon 120 to be pulled out of the sleeve 130, leaving the sleeve 130 in position within the intestine. Since the diameter of the deploying balloon 120 can be less than the diameter of the sleeve 130, deploying balloon 120 withdrawal is performed upon deflation and formation of a vacuum in the deploying balloon 120. As previously stated, a coating or lubrication may be placed between the sleeve 130 and the deploying balloon 120 during manufacture, to ensure easy deploying balloon 120 removal.

With reference now to FIGS. 9-13, there are illustrated another bariatric therapy system 300 in accordance with an embodiment of the present invention. System 300, in an embodiment, can include a delivery mechanism 315 and an implant device 305. As shown in FIGS. 9-13, the delivery mechanism 315 may be substantially similar to the delivery mechanism 115, 215 described above, but no separate housing may be necessary to deploy the device 305. The delivery mechanism 315, in an embodiment, may include a deploying balloon 320, similar to deploying balloon 120 and housing 110 in the embodiments described above, for use in the placement of device 305 at the site of implantation within the gastrointestinal tract. It should be noted that the length and shape of the deploying balloon 320 should be such that the balloon 320 can fit within the intestinal track. In an embodiment, the deploying balloon 320 may be formed from a continuous piece of material as shown in FIG. 9A. The deploying balloon 320 may also be formed from a soft and flexible material such that upon inflation of the balloon 320, the pressure therein can allow the device 305 to be advanced through the intestinal track. The material from which deploying balloon 320 can be made can also be inelastic to withstand a sufficient pressure for deploying the device 305. In an embodiment, the deploying balloon 320 may be formed from a single thin-walled membrane. For example, the deploying balloon 320 may be made from nylon laminated with polyurethane. In an embodiment, the deploying balloon 320 may have a thickness ranging from about 0.05 mm to about 0.09 mm. In an embodiment, the thickness of the deploying balloon 320 may be about 0.076 mm or 0.003 inches.

Figure 9A:
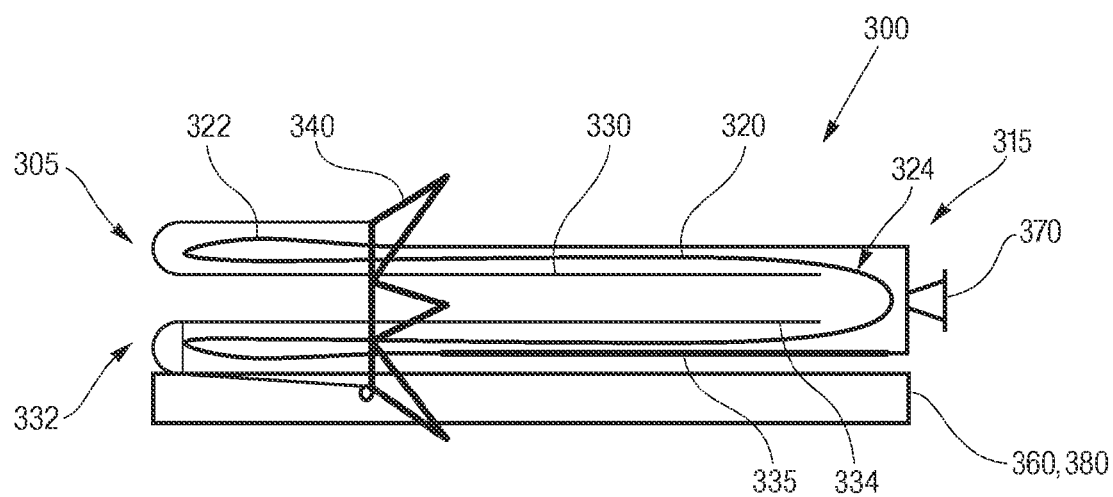
FIGS. 9A-9B, 10, 11, 12A-12C, and 13A-13B illustrate still another Intestinal Sleeve Delivery system in accordance with an embodiment of the present invention.

Referring still to FIG. 9A, the delivery mechanism 315, in an embodiment, may further include a sleeve 330 that may be positioned within deploying balloon 320, similar to the manner in which the sleeve 230 can be stored within deploying balloon 220, as described above. The sleeve 330, in one embodiment, may be formed from a membrane that can be less thick than the thickness of the membrane used to form the deploying balloon 320. In an example, the sleeve 330 may be approximately 0.025 mm (0.001") in thickness. The materials from which sleeve 330 may be formed includes without limitation, polyethylene, polyvinyl chloride, nylon, polyethylene terephthalate, or other polymer. The relative thickness of the intestinal sleeve 330 compared to the deploying balloon 320 can be important, as such thickness can provide less friction during eversion of the sleeve 330 and the deploying balloon 320. In one example, when a sleeve material has a thickness less than the thickness of the balloon material, air eversion may be possible and the everting structure may be sufficiently soft to advance through tortuous bowel. In one embodiment, a sleeve material can have a thickness that is about one-third of the thickness of the balloon material. In other examples, when a sleeve material has a substantially similar thickness to that of the balloon material, friction between the membrane layers may cause inflation pressure to rise to a sufficiently high level, such that an incompressible fluid (water or saline) may be required to deploy the sleeve 330. This may, in turn, cause increased rigidity of the everting closed ended balloon 320.

The device 305 may further include an anchoring mechanism 340 for anchoring and securing device 305 to a site of implantation. In an embodiment, anchoring mechanism 340 may be situated at proximal end 332 of sleeve 330. Anchoring mechanism 340 may be designed to be self-expanding and/or with a minimal profile so that when it is positioned within the stomach, the anchoring mechanism 340 can allow the stomach to retain substantially its full functional volume. In accordance with the embodiments shown in FIGS. 9-13, the anchoring mechanism 340 may be a self-expanding anchor or frame, for securing against the stomach wall. The anchoring mechanism 340, as shown in FIG. 10, may be a thin structure that can be designed to expand immediately proximal to the pylorus, and remains in the stomach, to allow the intestinal sleeve 330 to extend into the small intestine (e.g., into the duodenum and jejunum). The proximal end 332 of sleeve 330, in some embodiments, may be situated within the stomach just above the pylorus.

The anchoring mechanism 340, in one embodiment, may be constructed of spring metal, such as stainless steel, or it may be formed of a rigid plastic, such as polyurethane or polyethylene or polyethylene terephthalate. The anchoring mechanism 340 may be processed to have shape memory properties. The anchoring mechanism 340 may also be designed to present a smaller packing profile, as a thin frame can occupy less space than multiple layers of membrane in an inflatable anchor, and may present less obstruction to outflow of stomach contents.

Figure 11:
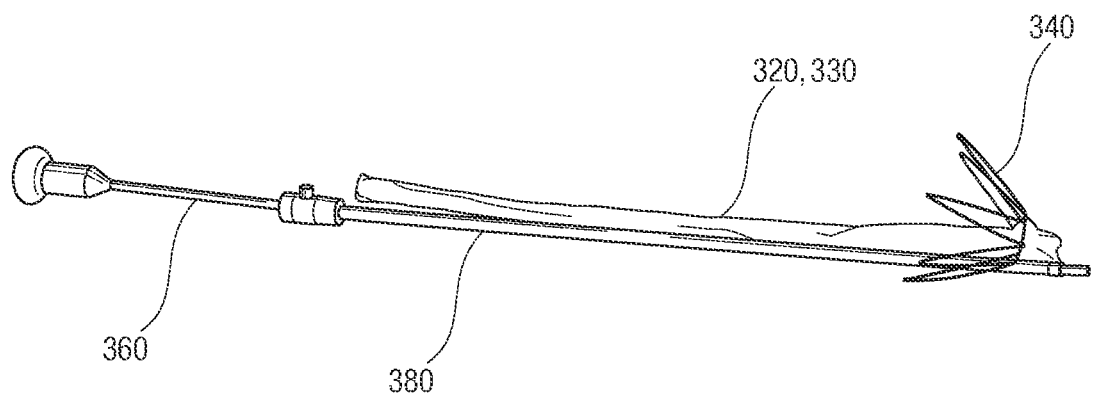

The system 300 may also be designed to accommodate a gastroscope 360. The gastroscope 360 may be used to provide or enhance columnal strength for advancement of the device into the duodenum in preparation for deployment of the intestinal sleeve in the bowel. In an embodiment, the gastroscope 360 can be a part of the system 300. The gastroscope 360 may be constructed from a plastic material such as polyethylene, polyethylene terephthalate, polyvinyl chloride, polyurethane, polytetrafluoroethylene (Teflon), or any other known strong material. In an embodiment, the gastroscope 360 may contain fiber or wire strands or braid for reinforcement. FIG. 11 shows a system 300 having gastroscope tube 380, gastroscope 360, anchor 340, and inverted deploying balloon 320 and sleeve 330.

The gastroscope 360, in an embodiment, may be provided within a gastroscope tube 380. The gastroscope 360 and/or tube 380 may be coupled to the deploying balloon 320, for example, through the use of a coupling mechanism 335, so as secure the device 305 thereto. The deploying balloon 320 may also be bonded to the gastroscope 360 and/or tube 380 to form a compact unit. The bonding, in an embodiment, can be along one line axially. In some embodiments, the gastroscope 360 and/or tube 380 may be coupled to the deploying balloon 320 through the use of an adhesive, such as glue or tape. In other embodiments, the gastroscope tube 360 and/or 380 may be coupled to the deploying balloon 320 through the use of a nail, screw, clip or other coupling mechanism 335 capable to bonding the gastroscope tube 360 and/or 380 to the balloon 320. Of course, those skilled in the art may appreciate that other coupling mechanisms 335 may also be possible as the present invention is not intended to be limited in this manner.

Figures 13A, 13B:
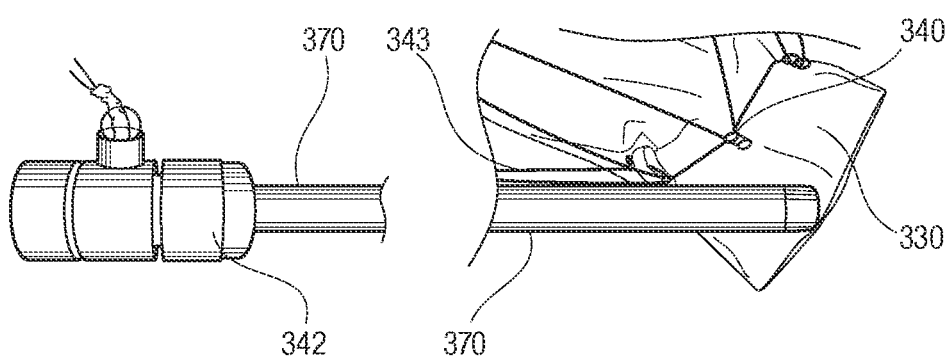

The gastroscope 360 may also contain a connecting mechanism 342, as shown in FIGS. 13A and 13B, for holding the anchoring mechanism 340 in position during deployment of the intestinal sleeve. The connecting mechanism 342 may be designed to couple the deploying balloon 320 to the gastroscope 360. In one embodiment, the connecting mechanism 342 may include a suture 343 to couple the deploying balloon 320 to the gastroscope 360. An opening in the side of the gastroscope 360 may be provided to allow the suture 343 to pass therethrough. As shown in FIG. 13B, the suture 343 may run the length of the gastroscope 360, out the side opening, through a loop in the anchoring mechanism 340, and end at a proximal port, to secure the anchoring mechanism 340 to the gastroscope 360. In an embodiment, the suture 343 may be designed so that it can be severed and removed so as to release the anchoring mechanism 340 and sleeve 330 following deployment. In another embodiment, the connecting mechanism 342 may further be designed to provide reference positioning for intestinal sleeve deployment.

Figure 12A:
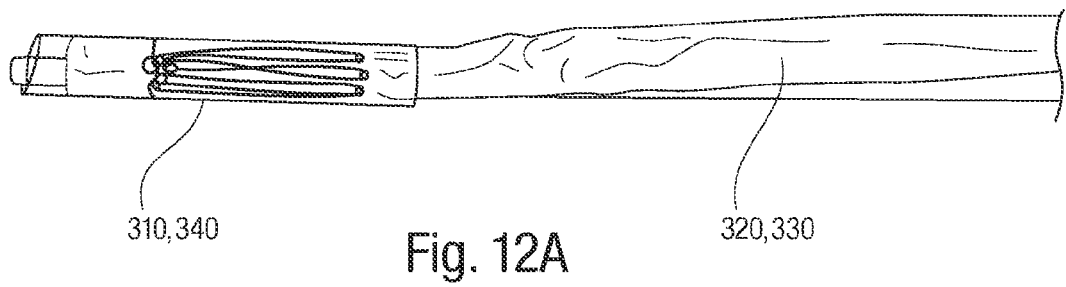
Figure 12B:
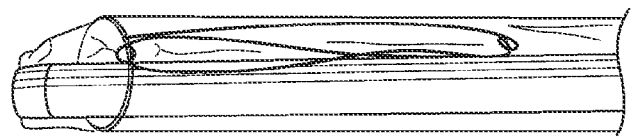
Figure 12C:
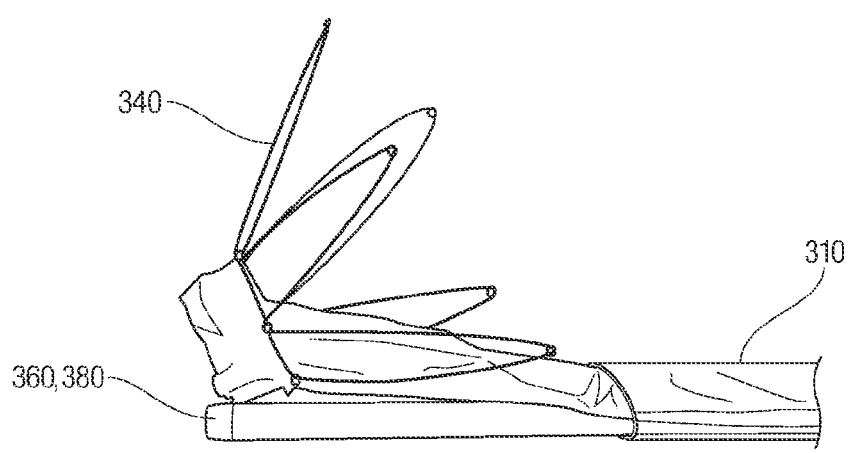

The system 300 of the present embodiment may further include a sheath 310, as shown in FIGS. 12A-12C, designed to for placement over the anchoring mechanism 340, the proximal end of deploying balloon 320, and the proximal end of the sleeve 330. The sheath 310 may be made from a semi-flexible material with a length sufficient to cover substantially the entire length of the anchoring mechanism 340. Of course, the length of sheath 310 can be varied according to specific designs. In an embodiment, sheath 310 can be sufficiently long so as to cover substantially the entire length of the deploying balloon 320 and sleeve 330. A wire 365 may be coupled to the sheath 310 and may extend substantially along the length of the device 305 or beyond. The wire 365 may be designed to be pulled, so as to withdraw the sheath 310 (prior to deployment of the sleeve 330) as illustrated in FIG. 12C, with the anchoring mechanism 340 in an expanded state.

Figure 9B:
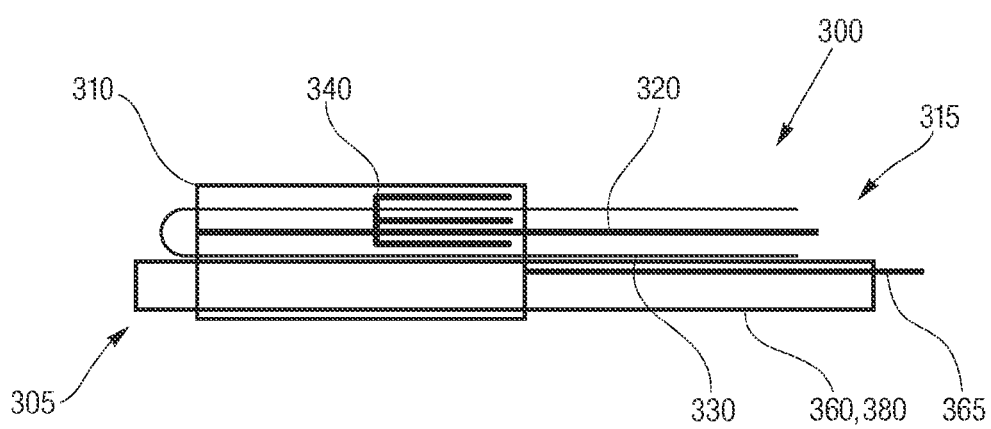
Figure 10:
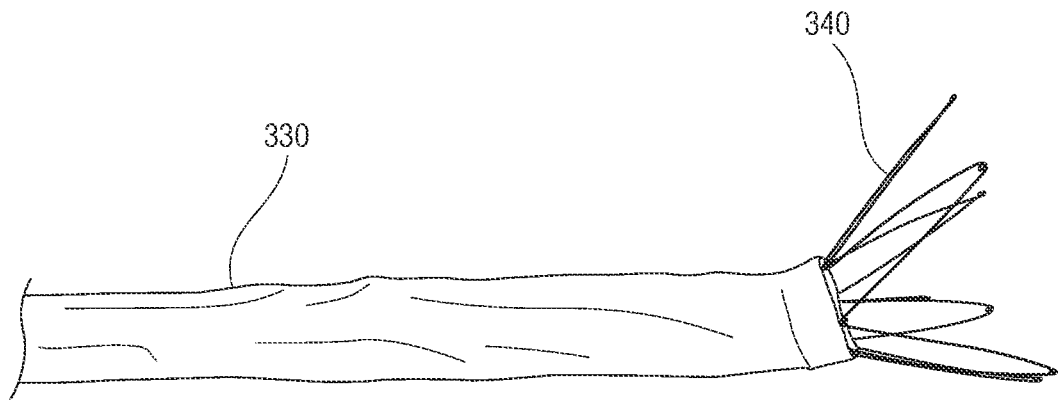

To deploy the gastrointestinal implant device 305, as shown in FIG. 9B, delivery mechanism 315 of system 300 may be provided with an inflation port 370. In an embodiment, the inflation port 370 may be designed to allow fluids (e.g., air, liquids, gas or other substances) to enter with sufficient pressure to evert deploying balloon 320 and deploy the gastrointestinal implant device 305. In one embodiment, inflation port 370 can be coupled to deploying balloon 320. Of course, other locations for the inflation port 370 are possible as long as fluids can enter delivery mechanism 315 with a sufficient force to deploy the device 305.

To prepare the delivery mechanism 315 for insertion in the body, a user can initially position an open ended sleeve 330 within deploying balloon 320. In an embodiment, the proximal end 332 of the sleeve 330 may be situated adjacent the open end 322 of the deploying balloon 320, while the distal end 334 of the sleeve 330 may be situated adjacent the closed end 324 of the deploying balloon 320. Additionally, anchoring mechanism 340, can be coupled to the proximal end 332 of the sleeve 330. The open ended sleeve 330, deploying balloon 320 and anchoring mechanism 340, in one embodiment, may be compressed and encased within sheath 310.

Once loaded, the delivery mechanism 315 may be inserted into the body, and advanced along the intestine within the body to a site of interest for implantation. The gastroscope 360 may be used to help guide the delivery mechanism 315 through the intestinal tract to a site of implantation. In an embodiment, a guidewire (not shown) may be used to maintain the stability of the delivery mechanism 315, as the delivery mechanism 315 advances through the tract. Once at the site of implantation, the delivery mechanism 315 can be prepared for deploying the device 305. Deployment may first require removal of the sheath 310 by pulling wire 365 to withdraw the sheath 310, prior to deployment of the sleeve 330, which may act to cause subsequent expansion of the anchoring mechanism 340. Expansion of the anchoring mechanism 340 can act to hold the gastrointestinal implant device 305 in a desired position during the eversion process. After the anchoring mechanism 340 is anchored to the stomach wall or intestinal wall at the site of interest, the sleeve 330 may be everted from within the deploying balloon 320. Eversion may require activation of the inflation port 350, which can result in the deploying balloon 320 being inflated. Inflation of the deploying balloon 320 can cause the deploying balloon 320 to enlarge and/or become pressurized, allowing the deploying balloon 320 to evert and deploy the device 305. In an embodiment, the deploying balloon 320 can provide a low friction compartment for everting the sleeve 330. With the gastrointestinal implant device 305 deployed and engaged within the intestinal wall, food and other food material can be passed through the sleeve 330.

Following deployment of the sleeve 330, the gastroscope 360, deploying balloon 320 and sheath 310 can be removed from the body. For example, the suture 343 may be severed and removed so as to release the anchoring mechanism 340 and sleeve 330 following deployment. In an embodiment, the deploying balloon 320 may be constricted to allow the deploying balloon 320 to be pulled out of the sleeve 330, leaving the sleeve 330 in position within the intestine. Since the diameter of the deploying balloon 320 can be less than the diameter of the sleeve 330, deploying balloon 320 withdrawal may be performed upon deflation and formation of a vacuum in the deploying balloon 320. As previously stated, a coating or layer of lubrication may be placed between the sleeve 330 and the deploying balloon 320 during manufacture, to ensure easy deploying balloon 320 removal.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A method for providing bariatric therapy comprising:
   directing an inverted sleeve accommodated within an inverted deploying balloon to a site of implantation, the sleeve having an open distal end;
   everting the inverted deploying balloon to evert the sleeve from an inverted position into a small intestine;
   anchoring the sleeve at its proximal end adjacent a pyloric junction with an anchoring mechanism; and allowing digested food to be directed from the stomach through the anchoring mechanism into the sleeve, while minimizing absorption of nutrients from the digested food by a wall of the small intestine.

2. The method of claim 1, wherein the everting step includes introducing positive pressure-into a housing in which the deploying balloon is situated to cause eversion of the deploying balloon from within the housing and eversion of the sleeve from within the deploying balloon.

3. The method of claim 1, wherein the anchoring step includes securing an anchoring mechanism coupled to a proximal end of the sleeve within the stomach so as to allow the sleeve to securely extend into the small intestine.

4. The method of claim 3, wherein in the anchoring step, the anchoring mechanism is an inflatable balloon sufficiently large to prevent the inflatable balloon from entry into the small intestine and to reduce the functional volume of the stomach in an inflated state.

5. The method of claim 3, wherein in the anchoring step, the anchoring mechanism is a self-expanding frame which, upon expansion, is frustoconical in shape for securing against a wall of the stomach while allowing the stomach to maintain a substantially full functional volume.

6. The method of claim 1, further including guiding the sleeve to a site of implantation with a gastroscope.

7. The method of claim 3, wherein the anchoring mechanism has a passageway therethrough for allowing digested food to be directed from the stomach into the sleeve.

8. The method of claim 7, wherein in the directing step, the deploying balloon is in an axial alignment with the passageway of the anchoring mechanism such that actuating the deploying balloon everts the open distal end of the sleeve through the passageway of the anchoring mechanism to implant the device.

* * * * *